United States Patent [19]

Draenert

[11] Patent Number: 4,671,263
[45] Date of Patent: Jun. 9, 1987

[54] DEVICE AND PROCESS FOR MIXING AND APPLYING BONE CEMENT

[76] Inventor: Klaus Draenert, Gabriel-Max-Str. 3, 8 Munich 90, Fed. Rep. of Germany

[21] Appl. No.: 753,174

[22] Filed: Jul. 9, 1985

[30] Foreign Application Priority Data

Jul. 11, 1984 [DE] Fed. Rep. of Germany ....... 3425566

[51] Int. Cl.⁴ .............................................. A61F 5/04
[52] U.S. Cl. ............................................. 128/92 VO
[58] Field of Search ............... 128/92 R, 92 E, 303 R, 128/92 G, 92 XP, 92 XO; 604/96–103

[56] References Cited

U.S. PATENT DOCUMENTS

| 2,970,973 | 2/1961 | Keryluk et al. | 128/92 R |
| 3,053,457 | 9/1962 | Trumbull et al. | 128/92 R |
| 4,227,184 | 7/1981 | Solomon | 128/92 R |
| 4,338,925 | 7/1982 | Miller | 128/92 E |
| 4,462,394 | 7/1984 | Jacobs | 128/92 C |
| 4,488,549 | 12/1984 | Lee et al. | 128/92 R |
| 4,546,767 | 10/1985 | Smith | 128/92 R |
| 4,576,152 | 3/1986 | Müller et al. | 128/92 R |

FOREIGN PATENT DOCUMENTS

| 45841 | 4/1928 | Fed. Rep. of Germany . |
| 1766334 | 3/1972 | Fed. Rep. of Germany . |
| 2814353 | 10/1978 | Fed. Rep. of Germany . |
| 7819584 | 10/1978 | Fed. Rep. of Germany . |
| 2733826 | 2/1979 | Fed. Rep. of Germany . |
| 2801706 | 7/1979 | Fed. Rep. of Germany . |
| 2905878 | 8/1980 | Fed. Rep. of Germany . |
| 2947875 | 6/1981 | Fed. Rep. of Germany . |
| WO85/04567 | 10/1985 | PCT Int'l Appl. . |
| 480075 | 12/1969 | Switzerland . |

OTHER PUBLICATIONS

Forschung und Fortbildung in der Chirurgie des Bewegungsapparates 1, zur Technik der Zementvwrankerung, K. Draenert, Art and Science Munchen, 1983.
Journal of Bone and Joint, vol. 65A, No. 9, Dec. 1983, pp. 1335-1338, Femoral Cement Compactor, Oh et al.

Primary Examiner—C. Fred Rosenbaum
Assistant Examiner—C. W. Shedd
Attorney, Agent, or Firm—Kinney & Lange

[57] ABSTRACT

The invention relates to a device and process for mixing and applying bone cement. The device comprises a sealable container (8) wherein the bone cement, prior to its application, is prepressurized at an adjustable pressure and from which it is subsequently applied at a controllable pressure. The device and the process of the invention allow bubble formation in the bone cement to be suppressed and to achieve the desired stratification of the bone cement around the prosthesis during application.

19 Claims, 7 Drawing Figures

DEVICE AND PROCESS FOR MIXING AND APPLYING BONE CEMENT

TECHNICAL FIELD OF THE INVENTION

The invention relates to a device and process for mixing and applying bone cement.

BACKGROUND OF THE INVENTION

In joint surgery it is common practice today to anchor components of replacement joints by using as bone cement a two-component resin which polymerizes during the operation at normal temperatures and which, on account of its plastic properties leads to an interlocking of the prosthesis component in the bony sheath. Because of its physical properties, the bone cement shrinks onto the prosthesis resulting in a closed metal-to-cement contact.

The bone cements commonly used are polymethylmethacrylate (PMMA) consisting of powdery bead polymers which are superficially dissolved by liquid monomers and embedded during the polymerization process. During mixing the polymer is immersed in the monomers. The PMMA beads are superficially dissolved and embedded in a composite manner. The processes during polymerization are explained in "Forschung und Fortbildung in der Chirurgie des Bewegungsapparates 1, zur Technik der Zementverankerung", K. Draenert, Art and Science Munich, 1983.

Such a composite structure can be compared with concrete, where air bubbles are likewise included during mixing. Moreover, when the monomer immerses the PMMA beads, filling defects remain. These defects are termed "lee phenomena". Furthermore, in the case of bone cements, the monomer liquid evaporates during the exothermic polymerization, whereby further bubbles are formed. The bubbles formed as mentioned above constitute the major part of the gas enclosures in bone cements.

The chemical reaction of the above-mentioned bone cements is initiated by a starter reaction, wherein, as a rule, dibenzoyl peroxide is activated by an activator such as p-aminotoluidine and then the radical chain polymerization is started. This polymerization proceeds exothermically. The monomer itself is stabilized by hydroquinone. Some bone cements are further stabilized by chlorophyll with simultaneous coloring. The storability of the monomer liquid can also be stabilized by vitamin C.

As a rule, the polymer powder or prepolymer is added to the monomer and mixed in a bowl using a spatula. In the processing phase following the mixing phase the bone cement is applied to the femoral medullary canal or to the bony acetabulum which are both prepared to anchor the cemented prosthesis components; the application is normally performed by hand and sometimes using a syringe. Such a syringe is described in DE-A-28 01 706, inter alia.

Using a syringe, the cement anchorage in the bone can be markedly improved. Therefore, so-called "cement compactors" have been proposed, the principle of which is to impact the cement in the plugged medullary canal to provide transverse anchorage. Such a cement compactor is described in "Journal of Bone and Joint", Vol. 65A, No. 9, December 83, pages 1335–1338.

Moreover, in order to prevent the evaporating monomer from producing unpleasant odors, containers have been proposed for storing and mixing the powder and liquid components, see for instance DE-A-28 01 706. Such containers constitute a closed system, but in practice the two components are all poorly mixed in comparison to cements prepared in the conventional manner with a bowl using a spatula.

Other proposals concern the problem of mixing the cement components and aim at improving the mechanical strength of the bone cement by improved mixing. Such a mixing vessel is described in DE-A-17 66 334. Said vessel has a ball separating the vessel into two chambers; this ball can be pressed through to move freely as a stirring means in one of the two chambers. While this principle may be applied in dental amalgams, it is not suitable for mixing bone cements, as the ball cannot be removed from the curing bone cement and the moving ball results in laminations of the increasingly highly viscous bone cements. Therefore, with this principle it is not possible to achieve uniformly mixed bone cements.

With cement syringes, the filling of the bone bedding is performed in different ways. On the one hand, filling is done from above in the downward direction, as described in the above-mentioned article in the "Journal of Bone and Joint", on the other hand, it is also performed in the other direction, i.e. upwardly from below, by means of a long nozzle, see DE-A-28 14 353.

While it is possible to build up some pressure in the cement by means of a nozzle as for instance described in DE-A-28 14 353, this is not so when applied to the bone, as the resistance of the nozzle reduces the pressure almost completely. With such a nozzle it is not possible to control the pressure during application. Another disadvantage of the nozzle is the so-called "tooth paste phenomenon", i.e. the emerging bone cement piles up like sausages, resulting in critical air, blood and marrow inclusions and laminations which very severely affect the mechanical strength of the applied cement.

All these proposals ultimately aimed at deep anchorage of the endoprostheses component in the bone and at thus improving the long term results of endoprosthesis replacement operations. While with the use of cement syringes the anchoring of the cemented prosthesis can be markedly improved, the mechanical strength of the bone cements thus achieved is still unsatisfactory as compared to bone cement samples prepared in laboratories.

It has been found that the "two-component" synthetic materials used as bone cement incorporate large and small bubbles which as loci minoris resistentiae constitute rated break points of the cement sheath surrounding the endoprosthesis. DE-A-28 14 353, has already disclosed attempts to compress the bone cements by means of appropriate devices during mixing in order to diminish the volume of enclosed air and to thus improve the mechanical strength of the bone cements. With the commercial syringes which in part comprise a one-way cartridge and a simple manually operated piston, it is also possible to render the bone cement somewhat more compact. The piston must not tightly seal the cylinder holding the bone cement in order that the air above the cement is not pressed into the cement. However, none of these known syringes fulfills this requirement, nor does any of these offer the possibility of closing the cement container in such a way that the cement can be exposed to high pressures. Where the ends of these syringes are sealable, these syringes all present the problem of enclosing air at both ends. On account of the laws of laminar flow, the air above the cement is centrally entrained in the cement mass and weakens the very part of the cement sheath that is later to enclose the metal prosthesis. It has been found that the enclosed air is by no means forced through the nozzle, but owing to the laminar flow is forced back laterally into the cement composition resulting in rated break points of the cement sheath.

This also applies to the process of preparing implant materials as described in EP-A-80 101 583, wherein the component mixture is somewhat compressed in a container that is not tightly sealable. Moreover, the pressure generated in this process cannot be adjusted and controlled precisely enough, nor is there sufficient time for handling and building up the pressure during application, in particular because curing proceeds rapidly. Nor does the piston described in DE-U 78 19 584, which fits tightly with the cylinder allow, the air above the cement to escape. Moreover, while the viscous bone cement can be forced out of the cylinder by the piston according to DE-U 78 19 584, the bone cement cannot be highly compressed with this piston. In addition, the lower end of the cylinder is open.

All of the syringes described have the disadvantage of not allowing pressures to build up in a short time and above all of not allowing them to be kept constant over a specific time and to be released quickly. In addition to not allowing high pressures to build up, all the known syringes which are manually compressed cause the muscles to fatigue quickly with the result that constant pressure is not ensured.

The injection piston according to DE-U 78 19 584, like the injection syringe according to DE-A-28 14 353, is at best suited for lamination-free injection of the cement into the bone, but not for effectively prepressurizing the cement to effectively suppress the afore-mentioned bubble formation. In most cases, the excess pressures achievable with the known devices operated manually or with support are by far less than 1 bar (about 100 kPa) and can at best be used to compress the large enclosed air bubbles produced during mixing. This, however, is not sufficient to substantially increase the mechanical strength of the bone cement.

Another problem originates from the fact that the long term success of the operation does not solely depend on the maximum mechanical strength of the bone cement. It is advantageous if the bone cement is somewhat porous at the interface to the bone. The porous surface of the cement enlarges substantially the contact area and histological findings have shown that bony ingrowth will occur as a function of the surface enlargement.

Pore formation can be largely controlled by different additives to the bone cements. However, experience has shown that the stability of the cements decreases with increasing porosity.

This means that any fillers diminish the mechanical strength of the cements resulting in a weakening of these cements if this is not compensated for by bone substance growing into the cement.

The solid (metal) endoprostheses used today place high demands on the cement sheath; it must prevent body liquid and granulating tissue from penetrating into the interface. On the other hand, as explained above, it has been found that bone material will grow from the bone-to-cement interface into the existing pores of the implant under favourable circumstances.

Moreover, it has been found that in conventional bone cements, the liquid monomer flows away quickly or evaporates at the interface to the blood-supplied bone, with the result that the polymerization of the polymer/monomer combination is disturbed and the bone cement especially weak at this point. Furthermore, the bone-to-cement interface is endangered by the fact that in this area, where there are no blood vessels, germs encounter especially favourable conditions for development at the cement surface. Moreover, it is necessary to reduce the polymerization temperature of the cement during surgery by adding fillers in order to prevent the bone from burning. The incorporation of blood and blood coagels results in laminated bone cements and in the formation of rated break points of the implant's cement sheath. By suitable fillers in this outer layer it is possible to achieve both haemostasis and infection prophylaxis as well as effective heat reduction. It is, however, a prerequisite that the mechanical strength of the metal implant's cement sheath is not adversely affected. For this reason, in full shaft implants, resorbable substances such as the tricalcium phosphate described in DE-A-29 05 878 are only suitable in the outer layer facing the bone. The same applies to additives such as the so-called "bone morphogenetic protein". The purpose of this invention is therefore to apply bone cement in such a way that the cement sheath around the metal prosthesis is as homogeneous and mechanically stable as possible and that the porosity of the surface facing the bone is determined by fillers.

SUMMARY OF THE INVENTION

It is an object of the invention to provide a device and a process for mixing and applying bone cement which make it possible to reduce the bubbles enclosed in the bone cement and to increase the mechanical strength of the bone cement.

It is another object of the invention to provide a device and process for mixing and applying bone cement which are meant to facilitate the desired stratification of the bone cement, and in particular the formation of a homogeneous cement sheath exhibiting increased mechanical strength around the prosthesis and an outer porous layer. The high pore volume of the outer layer ensures bony ingrowth into the cement and thus increases the pressure-transmitting surface of the bone.

The basic idea underlying the invention is to provide such a device which, firstly, permits tight sealing of the bubble-free bone cement during prepressurization at medium and high pressures, and secondly, the adjustable application of the bone cement at controllable pressures so that the bone is filled satisfactorily. Moreover, the device according to the invention makes it possible to achieve a stratification of the bone cement in the device prior to application and consequently the bone cement shows the desired distribution explained above following application.

The above-discussed problems are thus solved by the present invention.

DESCRIPTION OF PREFERRED EMBODIMENTS

The device of the invention includes a container for holding the bone cement prior to application and in particular during prepressurization; the container allows air to escape, on the one hand, and is hermetically and cement-tight sealable at high pressures, on the other hand. The container is constructed in such a way that the enclosed cement is prepressurized air-free at constant pressure and over a specified time, preferably during the entire prepressurization period. The pressure exerted on the bone cement can be precisely adjusted and controlled, so that pressures of from 2 bar (200 kPa) to about 20 bar (2 MPa) can build up.

The pressure may be generated manually by a motor, or by pressurized air. The pressure is transmitted to the cement by an ejector means, such as a pusher or piston, which is movable within the container. The ejector means seals the container at least cement-tight. Vents are provided to prevent the air above the bone cement from being pressed into the cement. Moreover, any air which might already be present in the bone cement on account of the mixing operation may escape through said vents. The air present at the distal end of the container is eliminated by loosening the closure cap.

In the device of the invention, the movable ejector means exerts pressures of between about 100 kPa to 2 MPa upon the curing bone cement composition while in contact therewith. In this way, it is possible to largely suppress the monomer evaporation during polymerization which, on account of the exothermic reaction, would take place if no pressure were applied. In addition, the air bubbles formed in the mixing phase are highly compressed, the bead polymers are better embedded and filling defects are avoided. Thus a very compact, composite material is obtained between the end of the mixing phase and the first third of the processing phase.

Moreover, the elevated pressure during prepressurization causes the chemical reactions in the bone cement to proceed completely. As a result, the residual monomer content is extremely low. Because of the higher filling density and more complete chemical polymerization the mechanical strength of the bone cement is considerably increased. Further advantages offered by the device of the invention are simple handling and safe application of the bone cement.

To control the pressure during prepressurization and application, a pressure gauge, such as a flat cylinder with a spiral spring and colored calibration, is preferably arranged in the pressurized zone; the pressure gauge is visible through a sterilizable window and the colour rings indicate the existing pressure. There may be provided specific color markings for the correct pressure in the pressurization and application phase. The described pressure gauge can also be situated at the rear of the piston and viewed at from the end of the syringe.

The pressure on the bone cement is preferably produced by compressed gases, such as pressurized air, which are introduced into a compression chamber via a conduit and which act on the rear end of the ejector means, such as a pushing stamp or a piston. Said ejector means is movable in the forward direction under pressure, and its circumference fits tightly with a casing, for instance a pressure cylinder. The pressure acting on the ejector is controllable by at least one valve. In the compression phase, a predetermined pressure is preferably adjusted, the pressure value depending on the viscosity of the bone cement. In the application phase, the pressure can be continuously controlled by the valve(s). The front part of the ejector extends into the cement container and fits so tightly with the inner wall of the cartridge that only air and no cement can escape between the two, once it is in contact with the bone cement.

In the pneumatic embodiment, the pressure in the conduit preferably ranges from 500 kPa to 1.5 MPa, and more preferably from about 800 kPa to 1 MPa. The pressure in the front part of the bone cement container is then from about 300 to 600 kPa.

In another embodiment, the pressure on the bone cement is produced either manually or with the aid of a motor, by turning a threaded rod after the ejector has reached the cement level. Thus, a pressure of about 400 to 800 kPa, preferably of about 500 to 600 kPa can be built up in the bone cement. In this embodiment the cement is also ejected manually or with the aid of a motor, by pushing the ejector means forward.

The above-mentioned pressure values are in each case to be understood as excess pressure relative to atmospheric pressure.

Vent means or air escapes are provided to prevent the enclosed air above the mixed and filled-in cement from being pressed into the cement during the compression phase. Preferably, these vent means are shaped as at least one axial longitudinal slot or as several openings spaced apart from each other in the axial direction of the container, for instance several rows of openings arranged in the axial direction, or they are shaped as valves. In order to allow the vent means to adapt exactly to the filling height of the cement, the container preferably exhibits a slidable outer jacket or sleeve capable of shutting or sealing part of the vent means.

In another embodiment, the air escapes are shaped as a lamellar cylinder mounted on the front part of the ejector. The lamellar structure or lamellar cylinder has at least one, preferably two to four, and most preferably three flexible lamellae, the crosssection of which corresponds approximately to the inner diameter of the cement container. During the forward movement of the ejector, the enclosed air above the cement can escape between the lamellae and the inner wall of the container. However, once the cement level is reached and the pressure is built up, the lamellae fit with the container so snugly that the cement cannot escape between the two. Optionally, the lamellae may also fit air-tightly with the inner wall of the container when they are in contact with the cement. In this way, the air can escape in a very simple manner before compression. The lamellar structure preferably consists of Teflon ® (Du Pont de Nemours and Co tradename for fluorocarbons of polytetrafluoroethylene and polyperfluoromethylene propylene).

During the compression phase, the container is sealed pressure-tight at its distal front end by means of a closure cap. Preferably, the closure cap is screwed on the container by means of a bayonet-type closure with rising thread so that the closed container is capable of withstanding pressures of up to about 2 MPa. In order to provide sterile conditions, the cement container preferably is a disposable container, for instance a disposable cartridge which can be mounted on the casing by a fast closure, such as a bayonet closure. The bayonet closure may be secured by a retaining nut.

In order to facilitate handling and application, the bone cement syringe is preferably shaped as a pistol, with the cement container, the piston and the compression chamber essentially forming the piston "barrel" and the valve control accommodated in the handle portion arranged essentially perpendicular to the "barrel".

Preferably, operation of the device of the invention is as follows: The bone cement is filled into the one-way container, the front, distal part of which is closed by a closure cap fitted with a bayonet closure with rising thread; the container is capable of withstanding pressures of at least about 2 MPa. The cap is at first loosely mounted so as to allow the distal air to escape. The cement previously prepared in a bowl is poured in its low viscosity phase into the container and the cylinder-shaped container is then pushed over the ejector and mounted to the casing with the bayonet closure. The ejector advances in the container as pressure builds up and forces the air above the cement to escape through the air escape openings arranged laterally and extending to the cement level or to flow backwards past the lamellae. These openings are adjusted to the appropriate amount of cement for instance by the outwardly slidable sleeve. The cap is tightly closed after the distal end of the container is vented.

In the embodiment where the container has air escape openings, the front part of the piston-shaped ejector is made to fit hermetically with the inner circumference of the cement container by means of a slider with sealing rings. In the embodiment exhibiting a lamellar structure, the lamellae fit with the inner circumference of the cement container so tightly that no cement can escape between the two, once the advancing ejector reaches the cement level and pressure has built up.

On account of the pressure increase, the column of cement is sealed by the closure cap and the cement is exposed to high compression approximately one minute after polymerization has started. Depending on the type of cement, the period of pressurization is from about 1.5 to 5 minutes after initiation of polymerization; the pressure is preferably kept constant. In the case of highly viscous cements, the period of pressurization is shorter. The pressures required to prevent bubble formation range from at least about 0.2 to 2 MPa, depending on the bone cements used. Where the compressed air installations are capable of only supplying pressures of up to 0.6 or 1.0 MPa, pressure intensifiers can be used.

During precompression, the ejector is mechanically or otherwise locked in order to keep the pressure constant. In the air-operated embodiment, the compression chamber is closed by operating one of the valves; in this position the valve can be temporarily fixed by a locking means, e.g. a lever. At the end of the prepressurization phase the compression chamber is relieved, preferably by operating two valves, i.e an unlocking valve and an air escape valve. This makes it possible for the closure cap of the one-way container to be removed. The bone cement is then pressed into the bone by means of the inlet valve at continuously adjustable pressures. Due to the possibility of sealing the medullary cavity of the femur, which is offered by the device of the invention, the device lends itself to all kinds of impacting.

According to the invention, the pressure exerted on the bone cement may be controlled in different ways; it is essential that during prepressurization the pressure exerted on the cement is higher and preferably constantly adjusted or controllable, while the pressure at which the cement is ejected when applied is lower and continuously adjustable. In one embodiment of the invention the pressure is controlled by means of at least two valves or sliders, which preferably have two switching positions each. By operation and locking of the first valve, the compression chamber is first highly pressurized in the prepressurization phase; it is advantageous for this pressure to be adjustable at the pressure source and to be predetermined. With the second valve, the first valve can be unlocked, the compression chamber closed and the air escape conduit opened. To relieve the compression chamber, both valves are operated. To control pressure during application, both valves are adjusted in such a way that both the inlet conduit and the air escape conduit are open; at least one of the two conduits is opened in a controlled manner by one of the two valves. Preferably, this control is achieved when the first valve is an inlet valve. In another embodiment one of the two valves, preferably the first inlet valve, may also be constructed as a pressure reducing valve. Moreover, the air may also escape via a third valve or by lifting or pressing a vent lever or button.

In accordance with the invention, the necessary functions in the pressure control may also be achieved by a single valve exhibiting at least 3 switch positions, providing for (1) constant high pressure in the compression chamber, (2) relief of the compression chamber and (3) continously adjustable pressure.

The stratification of the cement can be achieved by superimposing in the container of the invention two or more cement portions which have been prepared in different ways. The cement composition containing fillers is placed in the container as the lowest layer, making up for instance about one third or half of the total mass. Said layer is superimposed by a cement composition which was prepared separately; it is homogeneous and shows high density. The cement container can be closed at the lower end in the manner explained above, and can be fixed with the open end to the "barrel" of the syringe. The subsequent compression to which the cement is subjected does not result in a mixing of the layers.

The above-described desired stratification of the cement in the bone can be simply achieved and controlled in accordance with its formation by shaping the opening of the cylindrical cement container as an open truncated cone or frustum. The ratio of the opening at its front part to the diameter of the cylindrical container are specifically adjusted to each other. Depending on the viscosity of the cement and the desired layer thickness, the ratio of the cement container diameter to the front diameter of the opening is about 2:1 to 4:3, preferably 3:2. It is especially advantageous to render the front opening controllable by a shutter, for instance mountable caps; in this way the cement can be applied in a particularly controllable manner in accordance with the respective circumstances. Optionally, stratification can also be advantageously influenced by the choice of the truncated cone's angle of inclination.

The distal end of the container may also be constructed as a frustum which is not axially symmetric; its envelope surface is flattened on two sides and the top opening oval. This facilitates the application of the cement corresponding to the open end of the femur.

The stratification of the cement during application is achieved in such a way that the lower portion containing the fillers becomes anchored in large amounts at the proximal end of the femoral medullary canal, while the second homogeneous and dense portion is pushed centrally through the mass of the first layer towards the front and downwardly. The metal prosthesis is then pushed into the center of the cement composition and as a result of the laminar stratification the second cement portion settles around the metal to fit tightly therewith. This layer formation may be varied depending on the opening of the container. For instance, by selecting a very wide opening or a very small one, the outer layer will be very thick while the inner dense layer will be very thin, or conversely, the outer layer will be thin and the dense layer thick. This selection may be made in accordance with the viscosity of the cement and the type of prosthesis. The advantages of controlling the opening by shutters consist especially in the possibility of also making adjustments with respect to the shape of the proximal femur.

The above-mentioned results are reproducible with certainty also in cases where a prosthesis stocking is fitted around the stem to stabilize the cement sheath. In these cases the cartridge opening is centrally arranged in the stocking and the cement is injected into it. Here, too, a precise layer formation with a large porous outer layer and a dense inner sheath is obtained. The plasticity of the cement results in transverse anchorage by penetrating into transverse Volkmann canals. This is not adversely affected by the application of low viscous filler substances, because these fillers are removed like a coat when denser cement enters the Volkmann canals so that there is no loss of stability.

Instead of using one container, the different cements may also be prepared in two separate plastic cylinders in a closed system. To allow the air to escape, the two plastic cylinders are connected with each other in the axial direction via an adapter, for instance a quick closure (snap closure) exhibiting a rising bayonet thread; this allows the air to escape and provides a pressure-tight system.

With some fillers an especially advantageous layer formation can be achieved in different ways in accordance with the invention. Especially when the fillers all have a density higher than that of the bone cement, such as X-ray contrast media, sintered apatites or high density apatites, a coaxial rotation results in an ideal stratification within the container. In this case, the homogenous cement composition becomes the central portion during rotation while, on account of the centrifugal force, the heavier filler particles form the outer layers in the cement container. In accordance with the invention it is also possible to provide a cement syringe with a rotating cement container, for non-pressurized cements.

In a preferred embodiment of the device of the invention the device is suitable both for prepressurizing the bone cement to a high degree and for co-axial rotation. Compression and rotation can be produced especially advantageously by compressed gases, such as pressurized air. In addition, this process has the advantage of preparing the cement in one step in the usual manner. After closing the cartridge, the cement container with the composition is mounted to the applicator in the usual manner and the cement composition is pressurized by operating and locking the inlet valve. By closing the second valve, the compression chamber is kept under full compression. With the compression remaining constant, the cement container is then rotated axially, like an air driller, by means of a turbine-operated rotation mechanism via a by-pass valve, and preferably by further operating the inlet valve. An electromotor may also be provided as the drive for the rotation mechanism. In this case, however, it is more difficult to maintain sterile conditions.

With this embodiment of the device of the invention the bone cement can be prepressurized in the low viscosity phase and centrifuged. Here, the rotation axis is coaxial to the axis of the cement container; said coaxial rotation prevents the cement from unmixing, which would be the case in off-center rotation as in a laboratory centrifuge. After rotation, the heavy filler particles can therefore be found in the outer layers; after application the cement containing the filler particles forms the outer layer facing the bone, because of the laminar flow behaviour of the bone cement as described above. The central portion in the container is the homogeneous and dense cement composition which, after application, settles around the metal prosthesis.

Figure 1:
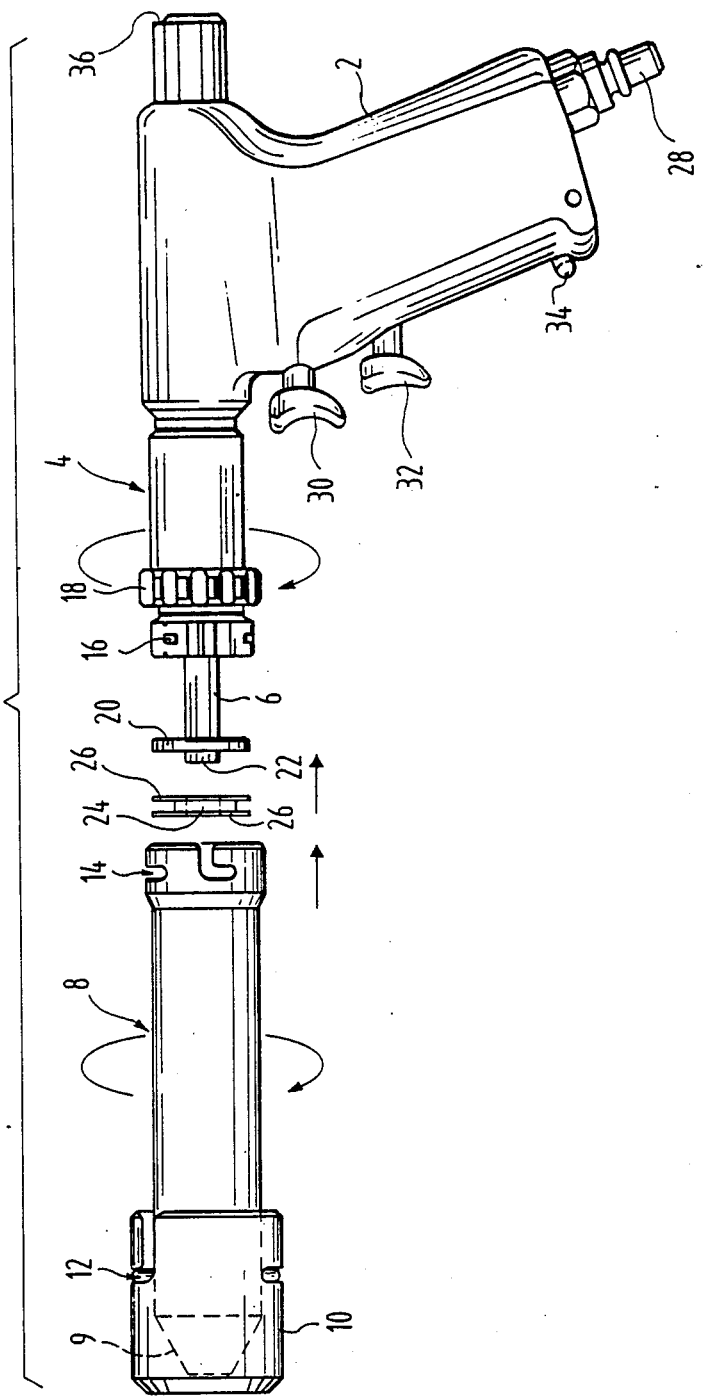
FIG. 1 is an overall view of the device according to the invention prior to assembly.

The air-operated bone cement pistol shown in FIG. 1 has a butt or handle 2, a casing 4, an ejector means 6, a bone cement container 8 with a conically tapered front part 9 and a closure cap 10. The container 8 and the closure cap 10 are connected with each other via a coupling, such as a bayonet closure 12. At the other end of container 8 a snap closure 14 is provided in the form of a bayonet thread which, when the bone cement pistol is mounted engages at the pins 16 located at the front part of casing 4 and connects container 8 with casing 4. Moreover, casing 4 is provided with a rotatable safety mechanism 18 for the bayonet closure 12.

The front part of the ejector means 6 is equipped with a slider 20 which has a short projection 22 with a smaller diameter. Projection 22 fits in an inner opening of a lamellar structure 24 exhibiting two flexible lamellae 26. The lamellar structure 24 is disposable.

The rear end of handle 2 is equipped with the compressed air connection 28 to be connected to a pressurized air source (not shown). Moreover, handle 2 is provided with a pressure inlet valve 30 formed as dosing valve, an unlocking valve 32 to unlock the pressure inlet valve 30 and a vent button 34. In the extension of casing 4, handle 2 comprises a colored pressure display 36.

The bone cement pistol in FIG. 1 is ready for assembly. After preparing the bone cement by adding the powder to the monomer and mixing the mass by stirring at a moderate speed, the bone cement is first filled into container 8 which is closed by closure cap 10. After mounting the lamellar structure 24 onto slider 20 of the ejector means 6, the bone cement pistol is assembled by locking the snap closure consisting of bayonet thread 14 and pins 16. The distal end of the container is vented by quickly operating valve 30, while cap 10 is still loosely mounted. Cap 10 is then firmly secured.

Then pressure inlet valve 30 is operated and locked. The compressed air supplied via compressed air connection 28 forces the ejector means 6 upon which the lamellar structure 24 is mounted to move in the container 8 in the forward direction, and as a result the air above the cement passes between the flexible lamellae 26 and the inner wall of casing 8. Once the lamellar structure 24 is in close contact with the cement in the container 8, the lamellae 26 fit with the inner surface of container 8 at least tightly enough so that no cement can pass between the two. For this purpose, the lamellar structure 24 preferably has three lamellae 26 in order to ensure an absolutely tight cement sealing. The bone cement is prepressurized at constant pressure from about the second to fourth minutes after polymerization has started. If the pressure supplied to connection 28 located, at the distal end of the container, is about 800 kPa, said constant pressure is about 300 to 500 kPa at the distal end of container 8.

Approximately five minutes after polymerization has started, the interior of the cement pistol is vented by unlocking valve 32 and pressing vent button 34. After the pressure is released, closure cap 10 can be removed. The bone cement can be applied by repeated operation of pressure inlet valve 30. In this case, pressure inlet valve 30 is not locked, and the pressure can be continuously adjusted. The pressure preferably ranges from about 100 to 200 kPa and pressure increase can be varied.

Figure 2:
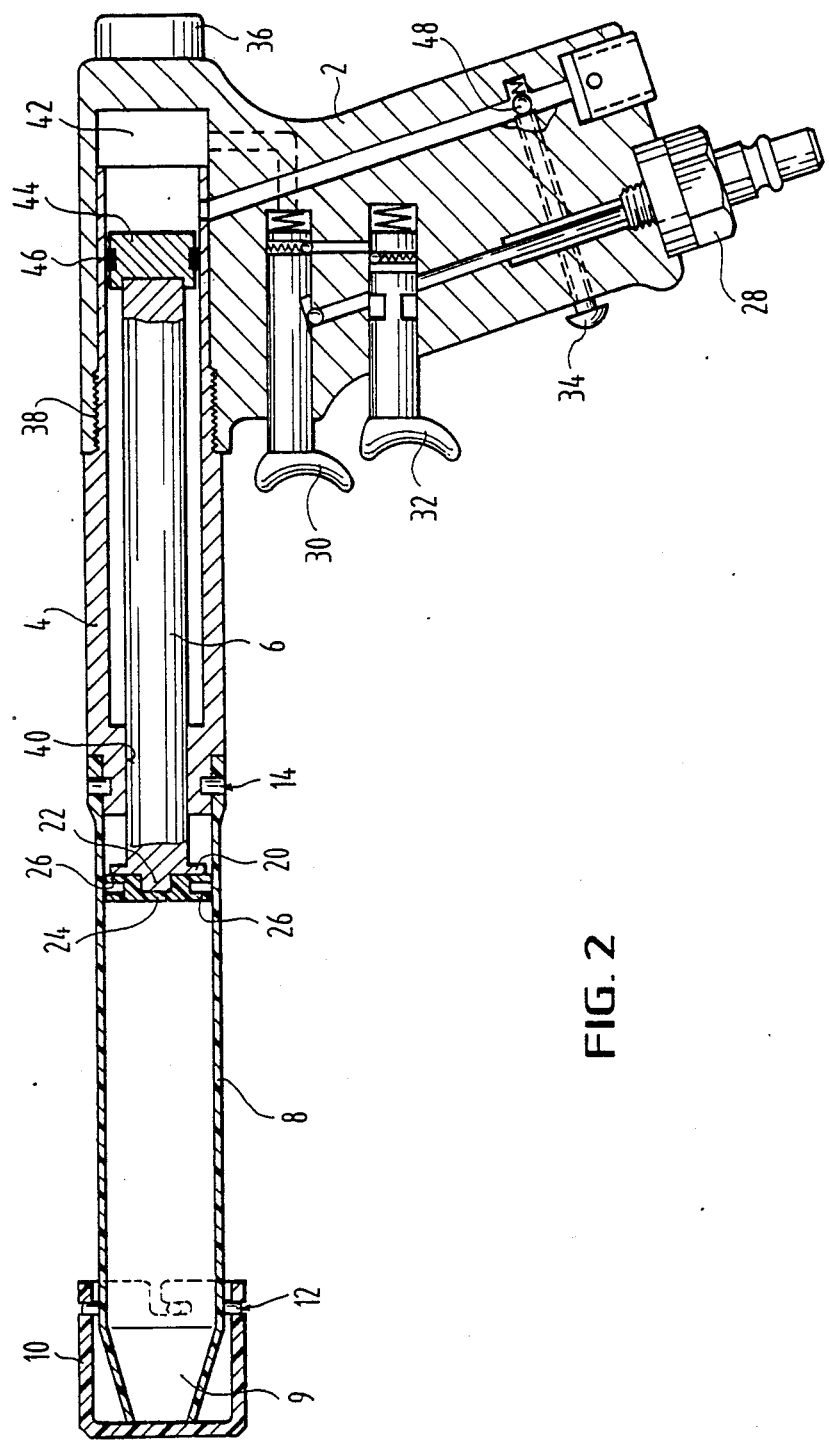
FIG. 2 shows the cross-section of a gas-operated embodiment of the device.

The apparatus depicted in FIG. 2, is a sectional view and essentially corresponds to the device of FIG. 1 after assembly.

Casing 4 is screwed onto handle 2 by means of thread 38 and has at its front part a piston guide 40 for the ejector means 6.

In the interior of handle 2 behind casing 4 there is a compression chamber 42 to be filled with compressed gas, such as pressurized air, or with a fluid supplied via connection 28 by operating pressure inlet valve 30. The ejector means 6 is equipped at its rear end with a rear slider 44. Said slider 44 has a sealing, for instance a sealing ring 46, fitting gas-tightly with the inner wall of casing 4, whereby compression chamber 42 is closed off pressure-tight from the rear end of the ejector means 6. Moreover, a vent valve 48 is provided by which compression chamber 42 is vented by operating button 34.

As can be seen from FIG. 2, the cone-shaped front part 9 of container 8 can be closed with closure cap 10 by means of a bayonet closure 12, whereby the pins provided on container 8 engage with the sloped bayonet thread. Bayonet closure 12 is pressure-tight up to a pressure of at least about 2 MPa. Container 8 and closure cap 10 are disposables and are preferably made of polymethylpentene.

During the forward movement of the ejector means 6 under the pressure of the compressed gases in compression chamber 42 at the beginning of the compression phase the enclosed air passes between the lamellae 26 of the lamellar structure 24 and the inner wall of container 8 into the rear part of container 8. The lamellae have a diameter of about 20 to 30 mm, preferably about 25 mm, and a thickness of about 0.5 to 1.5 mm, preferably about 1 mm. The individual lamellae 26, 26 are spaced about 1 to 2 mm apart. If during prepressurization the foremost lamella 26 is in contact with the cement column, the space between the lamellae 26 and the inner wall of container 8 is so small that the cement cannot escape between the lamellae 26 and the inner wall of container 8 and is compressed in the distal part of container 8 without air inclusion.

Figure 3:
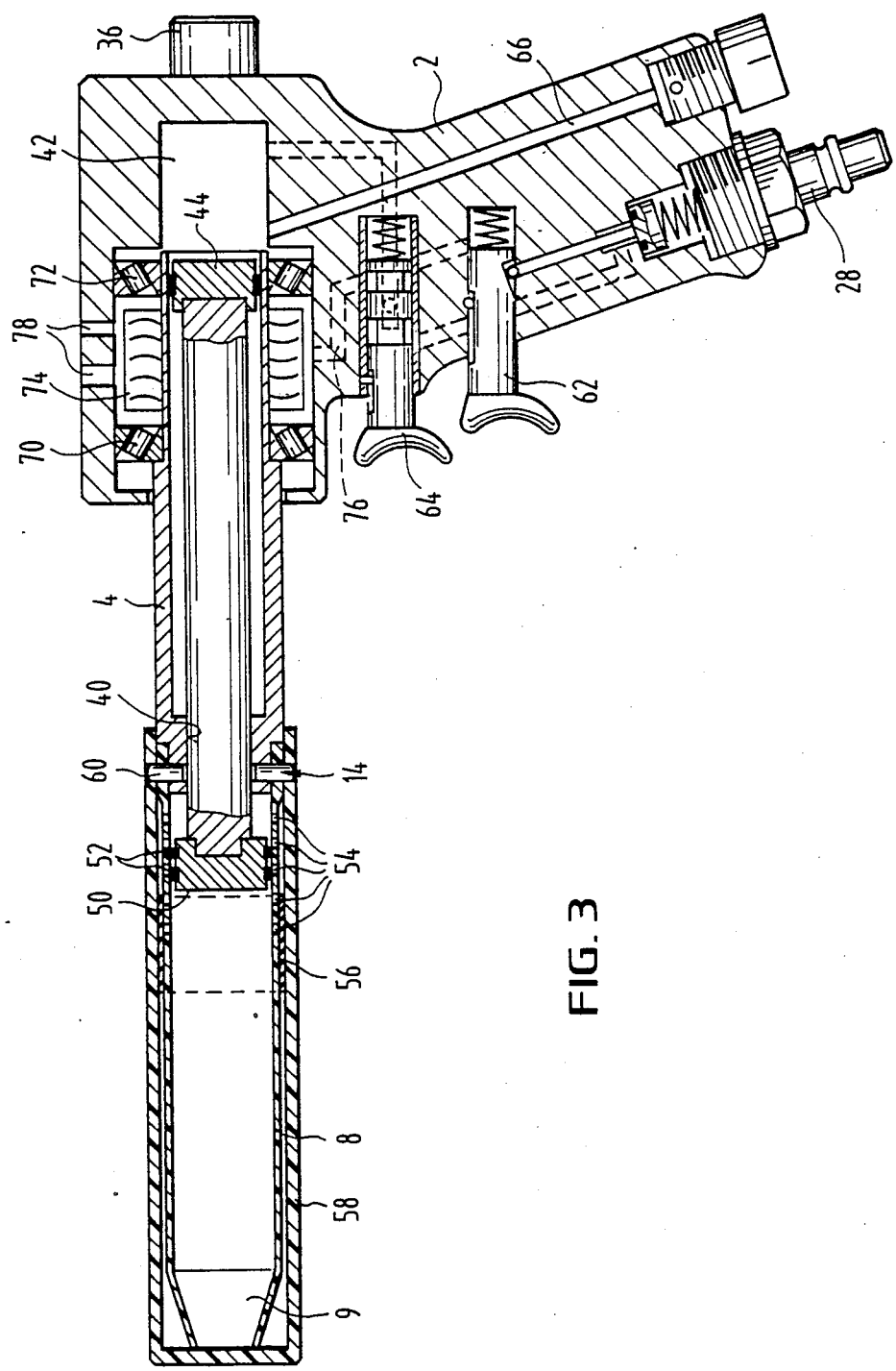
FIG. 3 is a cross-sectional view of another embodiment of the device exhibiting a rotation mechanism operated by pressurized gas.

The embodiment of the device of the invention according to FIG. 3 differs from the embodiment according to FIG. 2 in particular with respect to the design of the vent means, the closure cap and the pressure control. Moreover, in the embodiment according to FIG. 3, the cement can be coaxially rotated during prepressurization.

According to FIG. 3, the ejector means 6 has a front slider 50 with a sealing, such as sealing rings 52, which fit snugly and gas-tightly with the inner wall of container 8. The slider 50 of ejector 6 is made of a material, such as metal, synthetic material, ceramic material or Teflon ®, which is not superficially dissolved or attacked by methacrylate.

In its rear part, container 8 has several openings 54 which are axially spaced apart; there is slidable sleeve 56 over said openings which seals part of the openings 54 tightly enough so that no cement can escape.

Closure cap 58 covers container 8 almost entirely and catches with the snap closure 14 by means of pins 60.

In the embodiment according to FIG. 3, two valves 62 and 64 and an air escape conduit 66 are provided to control the pressure; the structure of the pressure control means is only being depicted schematically as in FIG. 2.

When the bone cement is prepared and applied, the ejector means 6 is first in the depicted rear position. Container 8 is filled with the prepared bone cement and after the distal air has escaped, cap 58 is firmly secured. By opening the pressure inlet valve 62, excess pressure is applied to the compression chamber 42 behind the ejector means 6. As a result, the ejector means 6 acting as a piston is further pushed into container 8. The air above the bone cement filled into the container is forced to escape laterally through openings 54, after movable sleeve 56 has been adjusted to the filling height of the cement. The ejector means 6 slides in the piston guide 40 until it is in close contact with the surface of the cement in container 8. The cement is now completely sealed in container 8 and is prepressurized at a predetermined constant value which is precisely adjusted in accordance with the cement used. This is preferably performed at the pressure source (not shown). At this stage of operation, the compression chamber 42 may be closed by the second valve 64. After prepressurization, the duration of which depends in particular on the viscosity of the cement to be compressed, the compression chamber 42 is relieved by operating the second valve 64, whereby air escape conduit 66 is opened. Cap 58 is then removed from container 8 and the bone cement can be pushed out by the ejector means 6 in a controlled manner by operating the inlet valve 62 and second valve 64. When applying the bone cement, valve 62 is not fixed; the pressure is adjusted manually to the desired value indicated by a color marking of the pressure gauge, said value ranging for example from 100 to 200 kPa. After applying the cement, the empty container 8 is removed and piston 6 is reset to its starting position.

The embodiment according to FIG. 3 also exhibits a rotation mechanism for rotating the cement. Here, casing 4 is fastened to handle 2 by means of a front angular roller bearing 70 and a rear angular roller bearing 72 to make it rotatable around its longitudinal axis. Casing 4 has a blade wheel 74 mounted onto it. Together with a valve-controlled compressed air conduit 76 and outlet openings 78, the blade wheel 74 forms a gas-operated turbine, by which casing 4 is rotated together with the ejector means 6 and the mounted container 8. To control the rotational movement, the inlet or outlet channel of the turbine may be provided with a valve. This valve is not shown in the drawing for the sake of simplicity. Preferably, the turbine has about 1,000 to 2,000 rpm.

In accordance with the invention, the device shown in FIG. 3 serves to prepressurize and rotate the bone cement either successively and/or simultaneously. Preferably, the bone cement is first prepressurized in the manner described above. Valves 62 and 64 are controlled in such a way that the turbine causes container 8 to rotate coaxially, while at the same time compression chamber 42 remains completely under pressure. Thus, with the device according to FIG. 3 the bone cement can be prepressurized and rotated at the same time in order to achieve a radial stratification of the cement in container 8. After prepressurization and rotation the pressure is released and the cement is applied in the manner described above.

The control means of valves 62 and 64 for building up pressure is only shown schematically in FIG. 3. Preferably, valve 62 has two positions. In the first position, the pressure supply to compression chamber 42 is opened, in the second position the compressed air conduit 76 of the turbine is opened. Optionally, in the second position the supply line to the compression chamber 42 may also remain open.

The embodiment with the lamellar structure as vent means according to FIGS. 1 and 2, may of course also be provided with the pressure control means, the larger closure cap and the additional rotation mechanism as the embodiment of FIG. 3.

Figure 4:
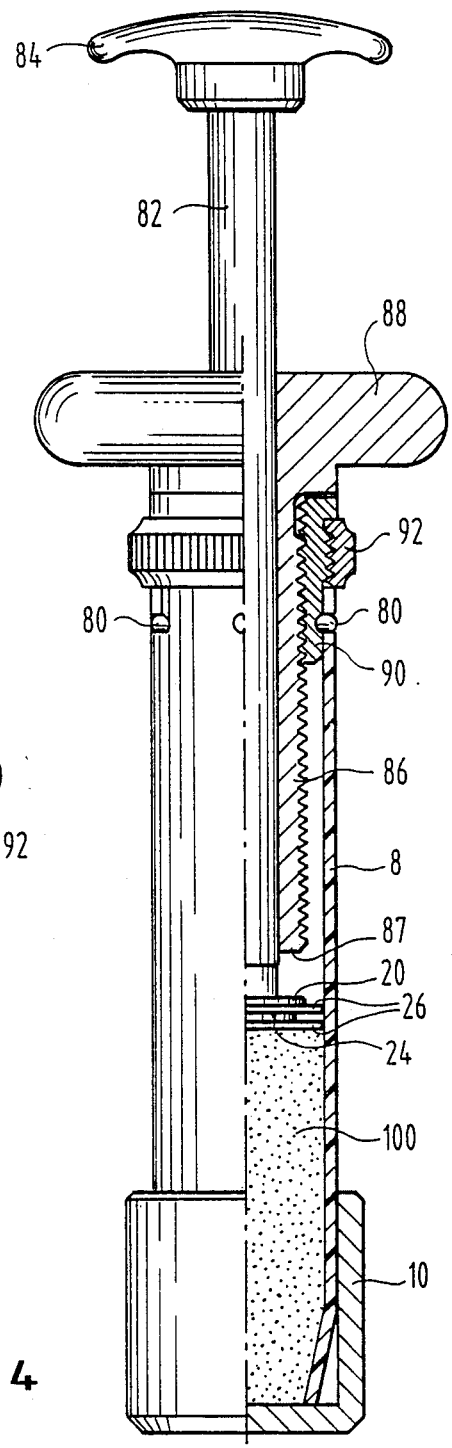
FIG. 4 is a part-sectioned view of an embodiment of the manually operated device.

FIG. 4 is a part-sectioned view of a manually operated embodiment of the device of the invention for applying bone cement. This embodiment is also equipped with a cartridge 8 to receive the bone cement and a removable closure cap 10 at its distal end. Cartridge 8 is fastened to the casing by cylinder pins 80.

The device exhibits an ejector means 82, the front part of which—as in the embodiment according to FIGS. 1 and 2—has a slider 20 on which a lamellar structure 24 with lamellae 26 is mounted. The rear end of the ejector means 82 is provided with an actuating means 84 for generating pressure manually. The middle part of the ejector means 82 can slide in rod 86 which is threaded externally, the rear end of the said rod being provided with a handle bar 88. The external thread of rod 86 engages with an internal thread of a guide piece 90. A knurled nut 92 is situated above guide piece 90.

When the bone cement is prepared and applied, the ejector means 88 is first drawn back. The container 8 is filled with the prepared bone cement and hooked to the cylinder pins 80. The closure cap 10 is mounted loosely initially and is not firmly secured until the distal end of the container 8 is vented and filled with bone cement. In FIG. 4, the bone cement is represented by reference sign 100.

The ejector means 82 is first moved in the container 8 in the forward direction by the actuating means 84, whereby the enclosed air passes backwards along the lamellae 26 until the foremost lamella 26 is in close contact with the surface of the cement (see FIG. 4). By turning the handle bar 88, the threaded rod 86 is moved forwardly within the internal thread of the guide piece 90, until the front part 87 of the threaded rod 86 comes into contact with the slider 20 of the ejector part 82. When the threaded rod 86 is turned further, the bone cement 100 is placed under pressure and prepressurized.

With this manually generated pressure, the pressure in the bone cement is likewise continuously adjustable. By completely turning the threaded rod 86 about twice in the guide piece 90 once the front part 87 is in contact with the slider 20, it is possible to generate at the distal end of the container an excess pressure of about 500 to 600 kPa in the bone cement. In this phase the pressure remains approximately constant, without further efforts on the surgeon's part.

After prepressurization, the bone cement is decompressed by resetting the threaded rod 86. The closure cap 10 is then removed and the bone cement can be applied in a controlled manner by sliding the ejector means 82 forward in the threaded rod 86. The forward movement of the ejector means 82 is performed as in a syringe, i.e. by holding the actuating means 84 and the handle bar 88 and pressing them towards each other.

The length of the threaded part of rod 86 is sufficient to ensure complete prepressurization even if the amount of cement is varied.

Both the prepressurization by turning the threaded rod 86 in the guide piece 90 and the application of the cement by pushing the ejector means 82 forward in the threaded rod 86 can be effected either manually or by means of a motor, e.g. an electric motor.

Figure 5:
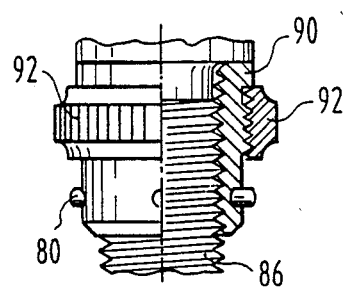
FIG. 5 shows a detail from FIG. 4.

FIG. 5 is a sectional view of part of FIG. 4 and shows the rod 86 with external threading, the guide piece 90 with internal threading and the knurled nut 92 by which the guide piece 90 can be secured and locked. It also shows four cylinder pins 80 which are each staggered by 90°.

In this embodiment, the outer diameter of the threaded rod 86 and the inner diameter of the guide piece 90 are preferably about 20 mm.

Figures 6, 7:
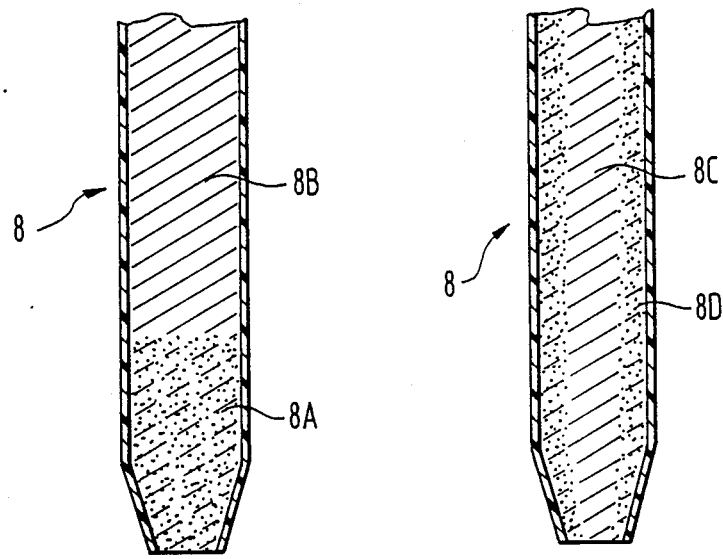
FIG. 6 shows a stratification of the cement composition into two layers, one near the bottom and one near the top of the container.
FIG. 7 illustrates a stratification of a more dense layer of cement and a less dense layer of cement caused by centrifugal force from rotating the conveyor.

FIG. 6 shows statification of the cement that can be achieved by superimposing in the container 8 two or more cement portions which have been prepared in different ways. A cement composition containing fillers is placed in the container as the lowest layer 8A, making up for instance about one-third or one-half of the total mass. The layer 8A is supermimposed by a cement composition 8B which was prepared separately and it is homogeneous and shows high density. The container can be closed at the lower end in the manner explained previously, and can be fixed with the open end of the barrel of the syringe. The subsequent compression to which the cement is subjected does not result any mixing of the layers.

FIG. 8, layer formation is achieved by coaxial rotation of the container 8 to result in an ideal stratification within the container. In this case, the homogeneous cement composition 8C becomes the central portion during rotation while, because of the centrifugal force, the heavier filler particles form the outer layers shown at 8D in the container 8.

I claim:

1. A device for mixing and applying bone cement, comprising
   a cylindrical container (8) to receive the bone cement prior to its application,
   an ejector means (6; 82) which is movable within the container (8) and fits cement-tight in said container (8),
   a removable closure cap (10; 58) whereby the container (8) can be closed tightly at its distal end,
   a pressure generating unit (42; 86) for prepressurizing the bone cement in the container (8) at an adjustable pressure and for applying the bone cement at controllable pressure, and
   vent means for letting the air above the bone cement escape while the ejector means (6; 82) moves in the container (8) in the forward direction.

2. The device according to claim 1, wherein the bone cement is placed under pressures of from about 200 kPa to about 2 MPa in the container (8).

3. The device according to claim 1, wherein the vent means are longitudinal slots and/or a plurality of axially spaced valves or openings (54) in the container (8).

4. The device according to claim 3, comprising a sleeve member (56) which is slidable on the container (8) in the axial direction.

5. The device according to claim 1, comprising a lamellar structure (24) mounted onto the ejector means (6) and having at least one flexible circular lamella (26), as vent means.

6. The device according to claim 1, wherein the container is disposable and can be secured to a casing by means of a fast closure.

7. The device according to claim 1, wherein the closure cap can be secured pressure-tight to the container by means of a sloped bayonet closure.

8. The device according to claim 1, comprising a compression chamber with an inlet for compressed gases, such as pressurized air, to exert pressure onto the ejector means, the pressure exerted onto the ejector means being controllable by at least one valve.

9. The device according to claim 1, comprising a rotary threaded rod for pressure generation.

10. The device according to claim 9, wherein the threaded rod is operated manually or by a motor.

11. The device according to claim 1, wherein the distal end of the cylindrical container has a tapered shape with an outlet opening.

12. The device according to claim 1, and means for selectively varying the size of the outlet opening of the distal end of the container while the bone cement is being applied.

13. The device according to claim 1, wherein the container consists of at least two cylinders which are axially aligned and can be connected with each other by an adapter.

14. The device according to claim 1, comprising a rotation mechanism for axially rotating the pressurized container with the bone cement.

15. The device according to claim 14, comprising a gas-operated turbine (74, 76, 78) for driving the rotation mechanism (70, 72) and valves (62, 64) at least one of which is formed by a by-pass valve and can be operated to connect the turbine (74, 76, 78) with the gas inlet.

16. The device according to claim 14, comprising a motor for driving the rotation mechanism (70, 72).

17. A process for mixing and applying bone cement comprising the steps of:
partially mixing bone cement powder and a liquid monomer to prepare the bone cement, filling the bone cement into a container, prepressurizing the bone cement in the container without air inclusion under a pressure sufficient to further mix the bone cement, decompressing the bone cement and applying the bone cement at a lower, precisely controllable pressure.

18. The process according to claim 17, including the steps of preparing a porous fraction of the bone cement containing fillers and a homogeneous fraction of the bone cement and superimposing the porous fraction and the homogeneous fraction of the bone cement in the container prior to prepressurization.

19. The process according to claim 17, including the step of rotating the bone cement containing fillers therein prior to application, so that a porous fraction containing the fillers and a homogeneous fraction of the bone cement are radially distributed in the container.

* * * * *